(12) United States Patent
Darnis et al.

(10) Patent No.: US 8,100,934 B2
(45) Date of Patent: Jan. 24, 2012

(54) DEVICE FOR OCCLUSION OF A CORPOREAL DUCT, IN PARTICULAR A VARICOSE VEIN

(75) Inventors: Thierry Darnis, Frans (FR); Alfredo Meneghin, Anse (FR); Rene Milleret, Montpellier (FR); Michel Therin, Lyons (FR)

(73) Assignee: Sofradim Production, Trevoux (FR)

( * ) Notice: Subject to any disclaimer, the term of this patent is extended or adjusted under 35 U.S.C. 154(b) by 462 days.

(21) Appl. No.: 10/492,084

(22) PCT Filed: Nov. 14, 2002

(86) PCT No.: PCT/FR02/03903
§ 371 (c)(1),
(2), (4) Date: May 10, 2004

(87) PCT Pub. No.: WO03/043506
PCT Pub. Date: May 30, 2003

(65) Prior Publication Data
US 2004/0254589 A1 Dec. 16, 2004

(30) Foreign Application Priority Data
Nov. 19, 2001 (FR) ...................................... 01 14803

(51) Int. Cl.
*A61M 29/00* (2006.01)
*A61B 17/08* (2006.01)

(52) U.S. Cl. ........................................ 606/200; 606/151

(58) Field of Classification Search .................. 606/151, 606/200, 72, 213, 228–230, 191; 623/13.11, 623/1.11, 1.5, 1.53; 424/443, 444, 423, 426; 604/264
See application file for complete search history.

(56) References Cited

U.S. PATENT DOCUMENTS

| | | | | |
|---|---|---|---|---|
| 3,276,448 A | * | 10/1966 | Kronenthal | 606/151 |
| 3,878,565 A | * | 4/1975 | Sauvage | 623/1.5 |
| 4,164,045 A | * | 8/1979 | Bokros et al. | 623/1.5 |
| 4,405,313 A | * | 9/1983 | Sisley et al. | 604/264 |
| 4,942,875 A | * | 7/1990 | Hlavacek et al. | 606/230 |
| 4,994,069 A | * | 2/1991 | Ritchart et al. | 606/191 |
| 5,019,093 A | * | 5/1991 | Kaplan et al. | 606/228 |
| 5,059,213 A | * | 10/1991 | Chesterfield et al. | 606/228 |
| 5,192,301 A | | 3/1993 | Kamiya et al. | |
| 5,310,407 A | | 5/1994 | Casale | |
| 5,382,259 A | * | 1/1995 | Phelps et al. | 606/151 |
| 5,628,756 A | * | 5/1997 | Barker et al. | 606/228 |
| 5,690,666 A | | 11/1997 | Berenstein et al. | |

(Continued)

FOREIGN PATENT DOCUMENTS

JP 03032677 * 2/1991

(Continued)

*Primary Examiner* — Julian Woo
(74) *Attorney, Agent, or Firm* — Carter, DeLuca, Farrell & Schmidt, LLP

(57) ABSTRACT

The invention concerns a device formed with several yarns (2) knitted together so as to constitute a cylindrical elongated knitted fabric, that is a knitted fabric wherein the yarns (2) forming the stitches intersect substantially at the radially inner zone of said knitted fabric. The invention also concerns a device for setting in place, in the corporeal duct to be treated, an occluding device (1), comprising a longitudinal tube designed to contain the occlusive device when the latter is inserted into the duct to be treated.

20 Claims, 2 Drawing Sheets

U.S. PATENT DOCUMENTS

| | | | |
|---|---|---|---|
| 5,792,154 A * | 8/1998 | Doan et al. | 606/151 |
| 5,833,705 A * | 11/1998 | Ken et al. | 606/191 |
| 5,911,731 A * | 6/1999 | Pham et al. | 606/191 |
| 5,925,060 A * | 7/1999 | Forber | 606/191 |
| 5,935,145 A * | 8/1999 | Villar et al. | 606/191 |

FOREIGN PATENT DOCUMENTS

| | | |
|---|---|---|
| WO | WO 94/09705 | 5/1994 |
| WO | WO 94/15534 | 7/1994 |
| WO | EP 0 800 791 A1 | 10/1997 |

* cited by examiner

DEVICE FOR OCCLUSION OF A CORPOREAL DUCT, IN PARTICULAR A VARICOSE VEIN

The present invention concerns a device for occlusion of a corporeal duct, in particular a varicose vein. The invention also concerns a device for positioning this occlusion device in this corporeal duct.

A varicose vein is usually treated by a technique called "stripping". This technique involves tearing the vein out using a cable or a probe. It has the disadvantage, however, of being painful and of being quite demanding to perform.

Techniques of endovenous treatment have also been considered.

The technique called CLOSURE uses a probe emitting radiofrequency waves, these waves causing heating of the wall of the vein, and thereby causing a lesion of the latter, which results in the obliteration of the vein. This technique permits effective control of the operating procedure and of the locally applied temperature, and it can be used on veins of up to 12 millimeters in diameter. However, it involves a risk of burning of the skin if the patient is thin, and it necessitates general or local anesthesia with heavy sedation because of the pain associated with it. Moreover, this technique is contra-indicated if the vein has severely dilated areas, and it cannot be used on the collateral veins or on the external saphenous vein, nor on the recurrent veins, and it is relatively expensive to perform.

The technique called EVLT uses a fiber optic connected to a laser. This technique is simpler to perform and less expensive. However, it involves risks of burning and has more painful sequelae than the above technique in view of the higher treatment temperature. In addition, this technique cannot be used on certain veins, such as the aneurysmal veins, the external saphenous vein or the collateral veins, and the cost of the laser is considerable.

Another technique consists in provoking sclerosis of the vein by introducing a substance in the form of foam. This technique is less expensive to perform and permits treatment of the collateral veins. However, it has the disadvantage that it is not possible to control the distribution of the sclerosant, the result of this being that there is greater risk of deep phlebitis and embolism. Moreover, this technique is less effective in terms of occlusion of the vein, given that it does not act on the collagen of the vessel wall, as is the case in the above techniques, but only on the endovenous zone. In addition, the reliability of the occlusion obtained is uncertain over the course of time, as repermeability of the treated vein is relatively common in the medium term.

The present invention aims to overcome all of the disadvantages of the existing techniques.

Its main object is therefore to make available an occlusion device which can be implanted using a procedure which is relatively simple and quick, and not difficult to perform, and which can be done under local anesthesia and induces minimal postoperative pain and few complications with regard to the tissues, in particular with regard to the nerves surrounding the saphenous veins.

Another object of the invention is to make available an occlusion device with extended possibilities of application, that is to say one that can be used for occlusion of the internal saphenous vein, but also of the external saphenous vein, and collateral veins of large caliber.

These objects are achieved by an occlusion device formed by several yarns knitted together so as to constitute a "cylindrical" elongate knitted fabric, that is to say a knitted fabric in which the yarns forming the stitches intersect substantially at the radially inner zone of this knitted fabric.

The device according to the invention thus has a mesh structure, meaning that it is compressible radially and very flexible longitudinally, and a "cylindrical" structure, meaning that the yarns are present at the radially inner zone of the device. The radial compressibility and the flexibility of the device permit easy introduction of this device into the duct to be treated, under simple local anesthesia, and do not generate any appreciable rigidity under the skin; the presence of the yarns at the radially inner zone of the device, along the entire length of the device, ensures reliable occlusion of the duct, along a considerable length thereof. In the case of a varicose vein, the occlusion device does not allow direct passage of blood over a length greater than one to a few stitches; the result of this is that the blood flow slows down, leading to thrombosis of the vein, which gradually organizes into fibrous tissue.

The occlusion device according to the invention therefore does not involve any heating of the treated corporeal duct and does not pose any risk of damage to the sensory nerves accompanying the veins. It can therefore be implanted using a procedure which is relatively simple and quick and not difficult to perform, and it can be used for a very wide range of indications, in particular for treating the external saphenous veins, the recurrent veins, and the collateral veins.

The device is preferably made up of yarns of absorbable material, preferably polylactic acid, polyglycolic acid, or a copolymer of these.

By virtue of the aforementioned mesh structure, the occlusion device has a very low weight/volume ratio (of the order of 0.02 to 0.08 grams per $cm^3$ according to the different sizes of devices), which allows it to occupy the whole volume of the duct with a small quantity of yarn per unit of length. This low quantity of yarn permits complete absorption of the occlusion device, without clinically significant inflammatory reaction. In the case of treatment of a varicose vein, once the fibrosis of the vein has taken place the macrophages absorb the hydrolyzed residues of the occlusion device and the fibrous thrombi; the vein finally reduces to a fibrous cord which will be eliminated by the organism, just as the lactic acid and/or glycolic acid is eliminated.

The absorbable material constituting the yarns of the occlusion device, the number of these yarns and the diameter of these yarns are advantageously determined in such a way that the period needed for absorption of the occlusion device is greater than or equal to the period of natural absorption of the treated corporeal duct once the occlusion has been performed.

The occlusion device can be made of warp stitches or weft stitches, and is preferably made of warp stitches.

The yarns forming the occlusion device are advantageously coated with one or more substances of a nature to promote occlusion and/or degeneration of the treated corporeal duct, or their surface is treated to increase their thrombogenicity. This may in particular involve a substance capable of irritating the wall of the duct so as to cause the latter to spasm around the device. In the case of treatment of a varicose vein, this spasm promotes occlusion of the vein and rapid onset of thrombosis. It may also involve clotting activators.

The occlusion device can additionally comprise at least one longitudinal yarn connected at its ends, forming a means acting against lengthening of this device when it is introduced into the longitudinal tube of the positioning device and during its positioning in the corporeal duct.

The device for positioning the aforementioned occlusion device comprises, according to the invention, a longitudinal tube able to contain the occlusion device at the time of implantation, grip means being provided to permit gripping of the occlusion device at one end of this tube, namely the distal end of the tube in relation to the orifice through which this tube has been introduced into the corporeal duct to be treated. The occlusion device can be loaded in advance in a longitudinal introducer tube or else can be "loaded" on the spot by the practitioner just before being placed in the corporeal duct of the patient. In this latter case, the positioning device comprises a system permitting the compression of the occlusion device and its introduction into the longitudinal tube.

The tube containing the occlusion device is introduced into the corporeal duct to be treated, then said grip means are used to grasp the occlusion device under the skin and maintain this occlusion device in place while the tube is withdrawn.

The positioning of the occlusion device can thus be performed particularly easily and quickly. Moreover, the tube has the advantage of effecting a relative aggression of the wall of the duct, which adds to the relative aggression of this wall subsequently caused by the occlusion device itself. In the case of a varicose vein, this aggression contributes to the rapid onset of thrombosis.

The tube is made of a material which is sufficiently rigid to permit engagement of this tube in the vein by sliding, but sufficiently flexible to cause no injury. This material can be, for example, polyethylene, PTFE, polyurethane, and, more generally, any polymer used in the medical field for production of catheters.

The diameter of the tube is advantageously smaller than that of the occlusion device in the uncompressed state of the latter.

The occlusion device thus makes it possible to place, in the corporeal duct, an occlusion device having, in the uncompressed state, a diameter equivalent to or slightly greater than that of this corporeal duct.

A sufficient density of yarn in the corporeal duct is thus obtained, which ensures occlusion of the duct under optimal conditions, and a degree of aggression of the wall of the duct, which contributes effectively to this occlusion.

The diameter of the occlusion device can in particular range from 4 to 9 mm depending on the veins to be treated, and the external diameter of the tube can range from 3 to 4.5 mm.

The grip means can be constituted by the yarns forming the occlusion device, in particular by knotting or other grouping together, in particular fusion, of these yarns at the distal end of the occlusion device. This means can also be formed by an atraumatic endpiece which is connected to the occlusion device, being able to be fitted at the distal end of the tube. After withdrawal of the tube, this endpiece is extracted from the patient's body through a distal incision and by separation from the occlusion device.

The proximal end of the tube can comprise a connector piece equipped with a hemostatic valve and with a lateral branch ending in a two-way or three-way cock, so as to permit injection of fluid inside the tube, either before the positioning of the occlusion device, or during this positioning. This proximal end of the tube can alternately comprise a Y-type connector with standard Luer lock ends.

A substance capable of causing sclerosis of the vein can in particular be injected in this way.

To ensure that it is clearly understood, the invention is again described below with reference to the attached diagrammatic drawing, which represents, by way of non-limiting examples, two possible embodiments of said occlusion device and device for repositioning this occlusion device.

FIG. 1 represents an occlusion device 1 permitting treatment of a varicose vein.

It is known that a varicose vein is a vein which is no longer able to prevent return of the blood in the direction of the extremity of the limb, that is to say in the direction of the foot in the case of a leg. This results in engorgement of the tissues, and, when the vein is very dilated, development of thromboses.

The varicose vein must therefore be treated so as to prevent circulation of the blood through it; since the veins form a network, the blood will then follow other veins for its circulation.

The device 1 is formed by five single yarns 2 of polylactic acid and/or polyglycolic acid which are knitted together so as to constitute a "cylindrical" elongate knitted fabric, that is to say a knitted fabric in which the yarns 2 intersect substantially at the radially inner zone of this knitted fabric.

Figure 2:
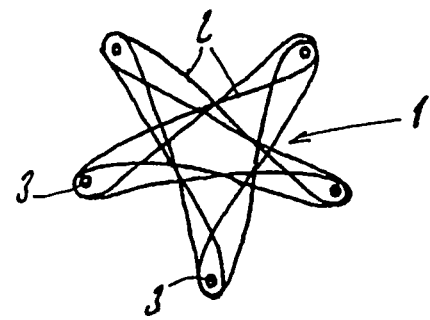
FIG. 2 is a very diagrammatic view of the needles of a knitting machine from which this device is obtained, and of the travel of the yarns feeding these needles.
Figure 3:
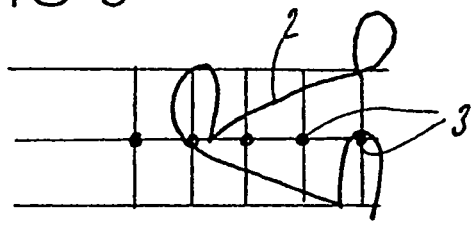
FIG. 3 is a view of the corresponding bonding grid.

Referring to FIGS. 2 and 3, it will be seen that this knitting is done on a circular knitting machine, which is a warp knitting machine. This knitting comprises warp stitches. The bonding is obtained by performing a wide sweep with the yarns 2, allowing them to jump several needles 3; a yarn 2 thus feeds a needle 3, then jumps several needles in order to feed a second needle 3 at an angular distance from the first needle, so that the portion of yarn 2 situated between these needles extends at the radially inner zone 4 of the circular surface delimited by the needles 3, which is also the radially inner zone of the device 1. In the example shown, the machine comprises five needles 3 which are each fed by a yarn 2. By the movement of the needle holder, a yarn 2 feeds a needle in an open stitch, then jumps two needles, so that it feeds the needle situated in fourth position with respect to this first needle, then returns to the first needle, and the cycle recommences.

Figure 1:
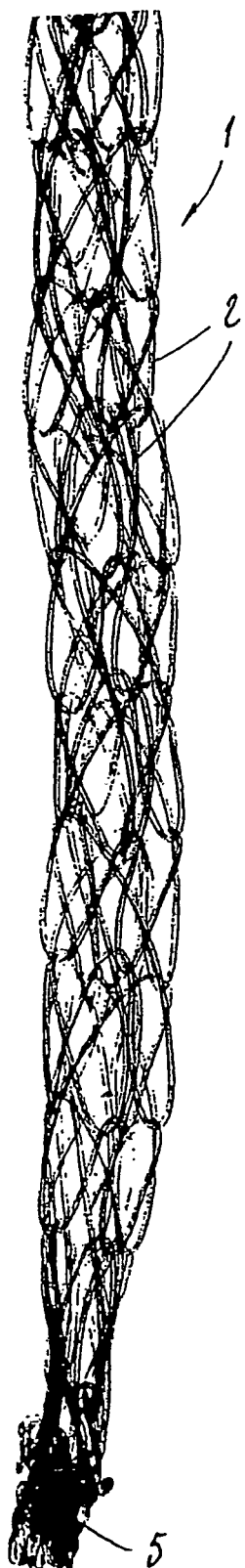
FIG. 1 is a side view of a portion of the occlusion device according to a first embodiment, this device, as represented, being enlarged by about four times.

As will be seen from FIG. 1, the knit thus obtained has a mesh structure, meaning that it is compressible radially and very flexible longitudinally, and a "cylindrical", that is to say non-tubular, structure, meaning that the yarns 2 are present at the radially inner zone of the device 1, this being the essential feature for the occlusive nature of the device 1.

At one end of the device 1, the yarns 2 are joined together, for example by thermal bonding, so as to constitute a grip zone 5 of more or less rounded shape. This zone 5 is dimensioned in such a way as to be able to be grasped through the skin, as will be explained below.

The device 1 is produced in a length sufficient to treat the entire length of a vein likely to be affected, for example 60 cm, and can be cut to the desired length. Thermosetting can be performed to limit the deformability of the stitches and to prevent any unraveling.

Moreover, to make it easier subsequently to introduce the occlusion device 1 into the positioning device 7, one or more yarns can be "descended" vertically at the center of the device 1 during the knitting phase. These unstitched yarns serve to limit the effect of traction during introduction of the occlusion device 1 into the positioning device 7, thereby also avoiding excessive deformation of the stitches. This longitudinal stitch or these longitudinal stitches also prevent lengthening of the device 1 during its deployment in the vein.

Figure 4:
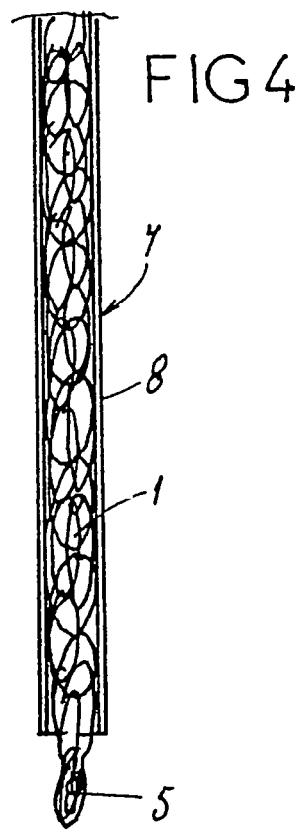
FIG. 4 is a longitudinal section of said positioning device, said occlusion device being engaged inside this positioning device.

Referring to FIG. 4, it will be seen that the device 7 for positioning the device 1 comprises a tube 8 which is able to contain this device 1, but with the zone 5 emerging from one end of this tube 8. This tube 8 is made of polyethylene and has a thickness such that it is sufficiently rigid to permit its engagement by sliding in the vein to be treated, but sufficiently flexible to cause no injury and to permit its easy advance through the sinuous vessels.

Figure 5:
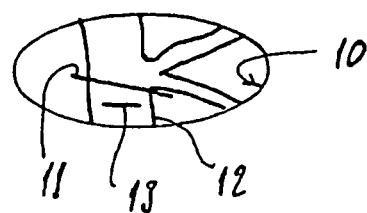
FIG. 5 is a view, on an enlarged scale, of an incision made in a leg, through which it is possible to expose the proximal part of the varicose vein to be treated.
Figure 6:
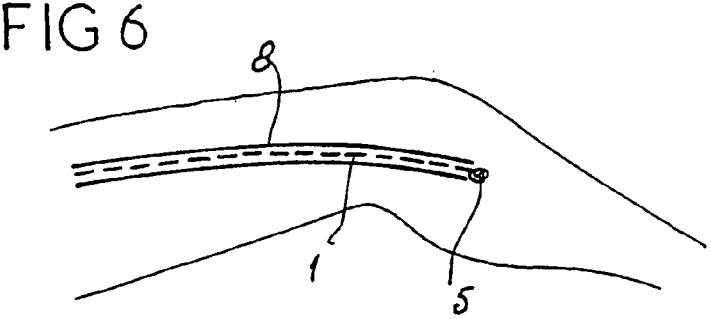
FIG. 6 is a view of the leg after engagement of the occlusion device and of the positioning device in the vein to be treated.
Figure 7:
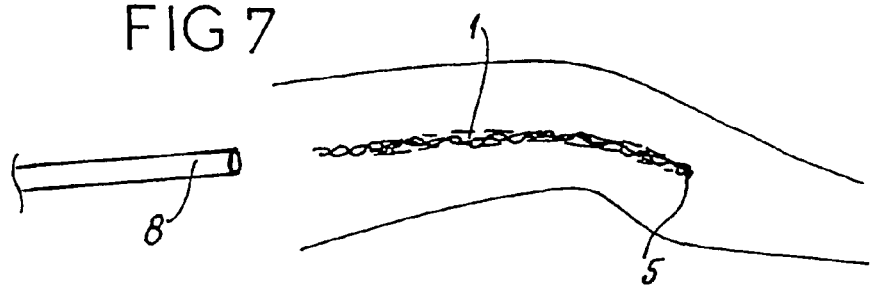
FIG. 7 is a view similar to FIG. 6, after withdrawal of the positioning device.

In practice, as is illustrated in FIGS. 5 through 7, an incision 10 is made in the leg in such a way as to expose the sapheno-femoral junction or to expose the external saphenous arch behind the knee; a non-absorbable ligature 11 is applied either at the sapheno-femoral junction, if blood reflux has been identified at this level, or below this junction, if drainage of the subcutaneous abdominal and pudendal veins is to be preserved; an incision 13 is then made in the vein 12 to be treated, below the ligature 11, and the device 7, into which the device 1 has been introduced in the aforementioned manner, is engaged in the vein 12 along the required length; once this engagement has been achieved, the zone 5 is grasped through the skin, then the tube 8 is withdrawn so as to release the device 1 in the vein 12; the incision 13 and then the incision 10 are closed.

Figure 8:
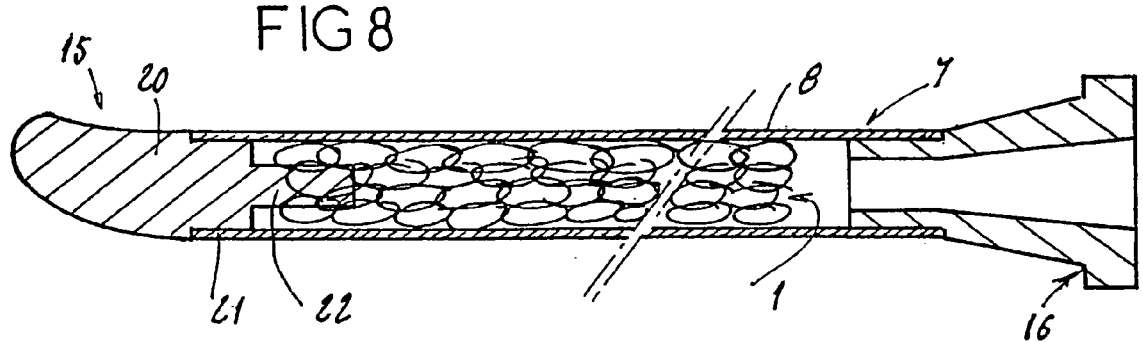
FIG. 8 is a view of the occlusion device and of the positioning device according to the second embodiment, in longitudinal section.

FIG. 8 shows diagrammatically a device 1 identical to the one just described, except that it does not have the zone 5, and also a device which comprises, in addition to the tube 8, a distal endpiece 15 and a proximal endpiece 16.

The endpiece 15 has a rounded portion 20, designed to be atraumatic, a circular portion 21 of slightly smaller diameter than the internal diameter of the tube 8, and an axial projection 22 with a hole running through it. The portion 21 can be engaged in the tube 8 and allows the endpiece 15 to be mounted on the distal end of the tube 8, while the projection 22 allows this endpiece 15 to be joined to the device 1.

This endpiece 15 fulfills the same function as the aforementioned zone 5. After withdrawal of the tube 8, it is removed from the patient's body through a distal incision and by separation from the device 1. It can also be made of a rapidly absorbable material, in which case it can be left in place.

In the example shown in FIG. 8, the endpiece 16 is of the Luer lock type. It can also be of the Y-shaped connector type with standard Luer lock ends. This endpiece 16 permits injection of fluid inside the tube 8, either before the positioning of the device 1 or during this positioning.

Figure 9:
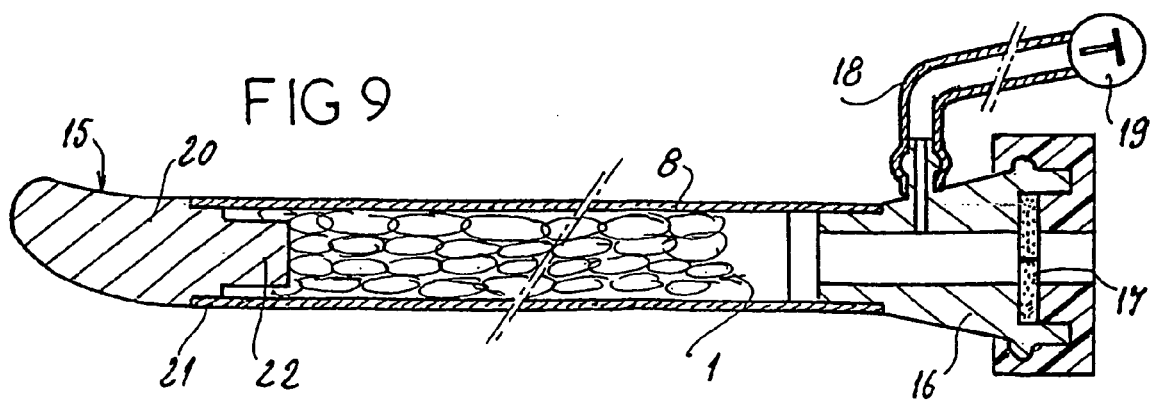
FIG. 9 is a view of the occlusion device and of the positioning device similar to FIG. 8, the positioning device having, at its proximal end, a connector socket different than that of the device shown in FIG. 8.

FIG. 9 shows a device 7 identical to that in FIG. 8, but with, at its proximal end, an endpiece 16 of the socket type with a hemostatic valve 17 and with a lateral branch 18 terminating at its end in a two-way or three-way cock 19. Fluid is injected through this lateral branch.

A substance able to provoke sclerosis of the vein 12 can in particular be injected in this way.

As will be evident from the foregoing, the invention affords a decisive improvement over the prior art by making available a device 1 for occlusion of a corporeal duct, in particular a varicose vein 12, which device can be implanted using a procedure which is relatively simple and quick and is not difficult to perform, and which procedure can be done under local anesthesia, causing minimal postoperative pain and few complications in respect of the tissues. This occlusion device additionally affords extended possibilities of application, that is to say it can be used for occlusion of the internal saphenous vein, but also of the external saphenous vein and collateral veins of large caliber.

It goes without saying that the invention is not limited to the embodiment described above by way of example, and that instead it covers all variant embodiments coming within the field of protection defined in the attached claims. Thus, the occlusion device can comprise six, eight or ten yarns in particular, the machine used then comprising six, eight or ten needles, respectively, and each yarn jumping two, three or four needles, respectively, during each cycle; the knitting can be done with warp stitches or weft stitches; the needles 3 can each be fed by one yarn 2 or by several yarns 2 if these yarns are double or triple; the yarns 2 can have their surfaces treated to increase their thrombogenicity; the occlusion device can be made of single-filament yarns or of single-filament and multi-filament yarns, with variable counts and sizes depending on the diameter of the occlusion device to be obtained, this diameter being adapted to the caliber of the type of vein to be treated.

The invention claimed is:

1. A corporeal duct occlusion device comprising:
a plurality of yarns knitted together so as to constitute a cylindrical, non-tubular elongate knitted fabric configured for insertion into a corporeal duct to slow blood flow through the duct and lead to thrombosis of the duct, the yarns forming stitches that intersect substantially at a radially inner zone of said knitted fabric;
wherein said device has a weight to volume ratio ranging from 0.02 to 0.08 grams per cubic centimeters.

2. The occlusion device as claimed in claim 1, wherein the yarns are made of an absorbable material.

3. The occlusion device as claimed in claim 2, wherein the number of the yarns and the diameter of the yarns are determined in such a way that the period needed for absorption of the occlusion device is greater than or equal to the period of natural absorption of the treated corporeal duct once the occlusion has been performed.

4. The occlusion device as claimed in claim 1, wherein the occlusion device is made of warp stitches.

5. The occlusion device as claimed in claim 1, wherein the yarns are coated with one or more substances of a nature to promote occlusion and/or degeneration of the treated corporeal duct, or their surface is treated to increase their thrombogenicity.

6. The occlusion device as claimed in claim 1, wherein thermosetting is performed in order to limit the deformability of the stitches and to prevent unraveling.

7. The occlusion device as claimed in claim 1, further comprising at least one longitudinal yarn connected at its ends, forming a means acting against lengthening of the occlusion device.

8. A device for positioning the occlusion device as claimed in claim 1, in the corporeal duct to be treated, comprising a longitudinal tube able to contain the occlusion device, grip means being provided on said occlusion device to permit gripping of the occlusion device at one end of this tube, namely the distal end of the tube in relation to the orifice through which this tube has been introduced into the corporeal duct to be treated.

9. The positioning device as claimed in claim 8, wherein the diameter of the tube is smaller than that of the occlusion device in an uncompressed state of the latter.

10. The positioning device as claimed in claim 8, wherein the grip means are constituted by the yarns forming the occlusion device at the distal end of the occlusion device.

11. The positioning device as claimed in claim 10, wherein the grip means is constituted by grouping the yarns together.

12. The positioning device as claimed in claim 11, wherein the grip means is constituted by grouping the yarns together through fusion.

13. The positioning device as claimed in claim 10, wherein the grip means is constituted by knotting the yarns together.

14. The positioning device as claimed in claim 8, wherein the grip means are formed by an atraumatic endpiece which is connected to the occlusion device, being able to be fitted at the distal end of the tube.

15. The positioning device as claimed in claim 8, wherein a proximal end of the tube comprises a connector socket.

16. The positioning device as claimed in claim 15, wherein the connector socket is a luer lock.

17. The occlusion device as claimed in claim 1, wherein the yarns are made from a material selected from a group consisting of polylactic acid, polyglycolic acid and copolymer.

18. The occlusion device as claimed in claim 1, wherein said device is flexible and radially compressible.

19. The occlusion device as claimed in claim 1, wherein said device further comprises a diameter in an uncompressed state ranging from 4 mm to 9 mm.

20. A corporeal duct occlusion device comprising:
a plurality of yarns knitted together so as to constitute a cylindrical, non-tubular, elongate knitted fabric, the yarns forming warp stitches that intersect substantially at a radially inner zone of said knitted fabric;
wherein said device has a diameter in an uncompressed state ranging from 4 mm to 9 mm and has a weight to volume ratio ranging from 0.02 to 0.08 grams per cubic centimeters,
wherein said device is configured and dimensioned to occlude fluid flow over a substantial portion of a length of said device.

* * * * *